United States Patent

Kober et al.

Patent Number: 5,158,598
Date of Patent: Oct. 27, 1992

[54] BITHIENYL DERIVATIVES, AND HERBICIDAL USE FOR AGENTS CONTAINING THEM

[75] Inventors: Reiner Kober, Fussgoenheim; Joachim Leyendecker, Ladenburg; Rainer Seele, Fussgoenheim; Klaus Fischer, Speyer; Hans Theobald, Limburgerhof; Bruno Wuerzer, Otterstadt; Karl-Otto Westphalen, Speyer; Norbert Meyer, Ladenburg, all of Fed. Rep. of Germany

[73] Assignee: BASF Aktiengesellschaft, Ludwigshafen, Fed. Rep. of Germany

[21] Appl. No.: 389,820

[22] Filed: Aug. 4, 1989

[30] Foreign Application Priority Data

Aug. 4, 1988 [DE] Fed. Rep. of Germany ....... 3826493
Mar. 3, 1989 [DE] Fed. Rep. of Germany ....... 3906811

[51] Int. Cl.$^5$ .................. C07D 409/14; A01N 43/10
[52] U.S. Cl. ........................................ 71/90; 548/225; 548/226; 548/233; 548/243; 548/245; 548/182; 548/183; 548/184; 548/203; 546/167
[58] Field of Search .............................. 546/167; 71/90; 548/203, 225, 226, 233, 243, 245, 182, 183, 184

[56] References Cited

U.S. PATENT DOCUMENTS

| | | | |
|---|---|---|---|
| 3,050,442 | 8/1962 | Bijloo et al. | 71/90 |
| 3,086,854 | 4/1963 | Harvey et al. | 71/2.5 |
| 3,268,543 | 8/1966 | Siegrist et al. | 260/304 |
| 4,319,026 | 3/1982 | Hedrich et al. | 71/90 |
| 4,769,062 | 9/1988 | Lange et al. | 71/90 |

FOREIGN PATENT DOCUMENTS

| | | | |
|---|---|---|---|
| 86/05949 | 10/1986 | PCT Int'l Appl. | |
| 495314 | 6/1976 | U.S.S.R. | 71/90 |
| 1268817 | 3/1972 | United Kingdom | |
| 1334015 | 10/1973 | United Kingdom | 71/90 |

Primary Examiner—David B. Springer
Attorney, Agent, or Firm—Keil & Weinkauf

[57] ABSTRACT

Bithienyl derivatives of the formula Ia

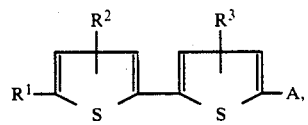

where the substituents have the following meanings:
$R^1$, $R^2$ hydrogen, halogen, nitro, formyl, $C_1$–$C_6$-alkyl, $C_1$–$C_6$-haloalkyl, $C_3$–$C_8$-cycloalkyl, $C_3$–$C_8$-cycloalkoxy, $C_1$–$C_6$-alkoxy, $C_1$–$C_4$-haloalkoxy, $C_1$–$C_4$-alkylthio, $C_1$–$C_4$-haloalkylthio, substituted or unsubstituted $C_1$–$C_6$-alkylcarbonyl, substituted or unsubstituted $C_3$–$C_6$-cycloalkylcarbonyl, substituted or unsubstituted $C_1$–$C_6$-alkoxycarbonyl and/or phenylcarbonyl;
$R^3$ hydrogen, halogen, $C_1$–$C_4$-alkyl, $C_1$–$C_4$-alkoxy, $C_1$–$C_4$-alkylthio, $C_1$–$C_4$-haloalkyl or $C_1$–$C_4$-haloalkoxy;
A —$CSNH_2$;
substituted or unsubstituted oxazol-2-yl, oxazol-5-yl, isoxazol-3-yl, pyrazol-3-yl, pyrazol-5-yl, thiazol-2-yl or a corresponding benzofused radical;
methods of manufacturing compounds Ia and agents containing a bithienyl derivative of the general formula I

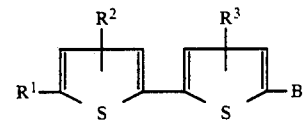

where
B is —$CSNH_2$;
substituted or unsubstituted pyridyl, quinolinyl, phenyl, naphthyl, furyl, pyrrolyl, pyrazolyl, imidazolyl, oxazolyl, isoxazolyl, thiazolyl or a corresponding benzofused radical.

6 Claims, No Drawings

BITHIENYL DERIVATIVES, AND HERBICIDAL USE FOR AGENTS CONTAINING THEM

The present invention relates to bithienyl derivatives of the formula Ia

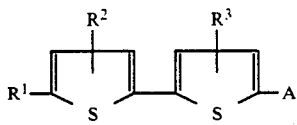

where
- $R^1$ and $R^2$ are each hydrogen, halogen, nitro, formyl, $C_1$-$C_6$-alkyl, $C_1$-$C_6$-haloalkyl, $C_3$-$C_8$-cycloalkyl, $C_3$-$C_8$-cycloalkoxy, $C_1$-$C_6$-alkoxy, $C_1$-$C_4$-haloalkoxy, $C_1$-$C_4$-alkylthio, $C_1$-$C_4$-haloalkylthio, $C_1$-$C_6$-alkylcarbonyl, which may be monosubstituted to trisubstituted by halogen atoms, or $C_3$-$C_6$-cycloalkylcarbonyl, which may be monosubstituted to trisubstituted by halogen and/or $C_1$-$C_4$-alkyl, or $C_1$-$C_6$-alkoxycarbonyl and/or phenylcarbonyl;
- $R^3$ is hydrogen, halogen, $C_1$-$C_4$-alkyl, $C_1$-$C_4$-alkoxy, $C_1$-$C_4$-alkylthio, $C_1$-$C_4$-haloalkyl or $C_1$-$C_4$-haloalkoxy;
- A is a radical —$CSNH_2$;
- oxazol-2-yl, oxazol-5-yl, isoxazol-3-yl, pyrazol-3-yl, pyrazol-5-yl, thiazol-2-yl or a corresponding benzofused radical, and these ring systems may carry one to five halogen atoms and/or one to three of the following substituents:
- $C_1$-$C_6$-alkyl, $C_1$-$C_6$-alkoxy or $C_1$-$C_6$-alkylthio, each of which may in turn be monosubstituted to pentasubstituted by halogen and/or monosubstituted by $C_1$-$C_4$-alkoxy, $C_1$-$C_4$-haloalkoxy, $C_1$-$C_4$-alkylthio, amino, $C_1$-$C_4$-alkylamino or di-$C_1$-$C_4$-alkylamino;
- $C_3$-$C_6$-cycloalkyl or phenyl, each of which may in turn be monosubstituted to pentasubstituted by halogen and/or monosubstituted to trisubstituted by $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
- a radical —$NR^4R^5$ or
- a radical —$COR^6$;
- $R^4$ and $R^5$ are each hydrogen, formyl, $C_1$-$C_6$-alkyl, $C_1$-$C_6$-haloalkyl, $C_1$-$C_4$-alkoxy, $C_1$-$C_4$-haloalkoxy, $C_1$-$C_6$-alkylcarbonyl, which may be monosubstituted to trisubstituted in the alkyl moiety by halogen, or $C_1$-$C_6$-alkoxycarbonyl and/or phenylcarbonyl, which may in turn be monosubstituted to pentasubstituted by halogen and/or monosubstituted to trisubstituted by $C_1$-$C_4$-alkyl, $C_1$-$C_4$-haloalkyl, $C_1$-$C_4$-alkoxy or $C_1$-$C_4$-haloalkoxy,
- $R^6$ is hydroxyl, $C_1$-$C_6$-alkoxy, $C_1$-$C_4$-alkoxy-$C_1$-$C_4$-alkoxy, $C_3$-$C_6$-alkenyloxy, $C_3$-$C_6$-alkynyloxy, phenoxy or benzyloxy, and the aromatic rings may in turn be monosubstituted to pentasubstituted by halogen and/or monosubstituted to trisubstituted by $C_1$-$C_4$-alkyl, $C_1$-$C_4$-haloalkyl, $C_1$-$C_4$-alkoxy or $C_1$-$C_4$-haloalkoxy, or a group —$NR^7R^8$, and
- $R^7$ and $R^8$ are each hydrogen, $C_1$-$C_6$-alkyl, $C_3$-$C_6$-alkenyl, $C_3$-$C_6$-alkynyl, $C_1$-$C_4$-alkoxy-$C_1$-$C_4$-alkyl, phenyl or benzyl.

The present invention furthermore relates to processes for the preparation of compounds Ia and herbicides which contain a bithienyl derivative of the formula I

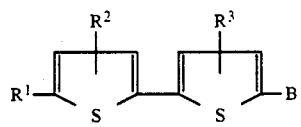

where
- $R^1$, $R^2$ and $R^3$ have the abovementioned meanings,
- B is a group —$CSNH_2$,
- pyridyl or quinolinyl, which may carry one to three of the groups stated for $R^3$;
- phenyl or naphthyl, which may carry one to three of the following radicals: halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_2$-$C_6$-alkenyl, $C_2$-$C_6$-alkynyl, nitro and/or cyano;
- furyl, pyrrolyl, pyrazolyl, imidazolyl, oxazolyl, isoxazolyl, thiazolyl or a corresponding benzofused radical, and these ring systems may carry one to five halogen atoms and/or one to three of the following substituents:
- $C_1$-$C_6$-alkyl, $C_1$-$C_6$-alkoxy or $C_1$-$C_6$-alkylthio, each of which may in turn be monosubstituted to pentasubstituted by halogen and/or monosubstituted by $C_1$-$C_4$-alkoxy, $C_1$-$C_4$-haloalkoxy, $C_1$-$C_4$-alkylthio, amino, $C_1$-$C_4$-alkylamino or di-$C_1$-$C_4$-alkylamino;
- $C_3$-$C_6$-cycloalkyl or phenyl, each of which may in turn be monosubstituted to pentasubstituted by halogen and/or monosubstituted to trisubstituted by $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
- a radical —$NR^4R^5$ or
- a radical —$COR^6$;
- $R^4$ and $R^5$ are each hydrogen, formyl, $C_1$-$C_6$-alkyl, $C_1$-$C_6$-haloalkyl, $C_1$-$C_4$-alkoxy, $C_1$-$C_4$-haloalkoxy, $C_1$-$C_6$-alkylcarbonyl, which may be monosubstituted to trisubstituted in the alkyl moiety by halogen, or $C_1$-$C_6$-alkoxycarbonyl and/or phenylcarbonyl, which may in turn be monosubstituted to pentasubstituted by halogen and/or monosubstituted to trisubstituted by $C_1$-$C_4$-alkyl, $C_1$-$C_4$-haloalkyl, $C_1$-$C_4$-alkoxy, or $C_1$-$C_4$-haloalkoxy,
- $R^6$ is hydroxyl, $C_1$-$C_6$-alkoxy, $C_1$-$C_4$-alkoxy-$C_1$-$C_4$-alkoxy, $C_3$-$C_6$-alkenyloxy, $C_3$-$C_6$-alkynyloxy, phenoxy or benzyloxy, and the aromatic rings may in turn be monosubstituted to pentasubstituted by halogen and/or monosubstituted to trisubstituted by $C_1$-$C_4$-alkyl, $C_1$-$C_4$-haloalkyl, $C_1$-$C_4$-alkoxy or $C_1$-$C_4$-haloalkoxy; or a group —$NR^7R^8$, and
- $R^7$ and $R^8$ are each hydrogen, $C_1$-$C_6$-alkyl, $C_3$-$C_6$-alkenyl, $C_3$-$C_6$-alkynyl, $C_1$-$C_4$-alkoxy-$C_1$-$C_4$-alkyl, phenyl or benzyl.

Nematocidal substances, including those of the formula I'

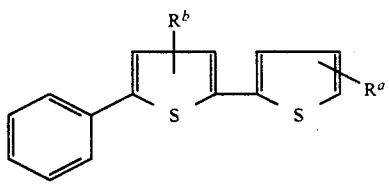

where $R^a$ and $R^b$ independently of one another are each, for example, hydrogen, alkyl, an aliphatic acyl group, halogen and/or nitro, are disclosed in U.S. Pat. No. 3,050,442.

In addition to the novel insecticidal property, reference is also made there to phytotoxic effects, which are demonstrated for α-bithienyl and α-terthienyl in experimental examples.

Furthermore, WO-A 86/05949 describes phenylbithienyl derivatives I″

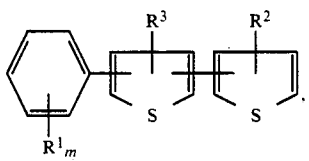

the general definition of whose radicals and indices is covered by the phenylbithienyl derivatives I. These compounds are recommended as insecticides and acaricides, and it is expressly pointed out that there were no problems with the phytotoxicity at the application rates used (from 50 to 750, preferably from 150 to 500, g/ha) under the experimental conditions.

It is an object of the invention to provide bithienyl derivatives and herbicides which have high selectivity at a low application rate, i.e. control undesirable plants without damaging the crops.

We have found that this object is achieved by the compounds Ia defined at the outset and herbicides containing the bithienyl derivatives I defined at the outset.

The majority of bithienyl derivatives I are known or can be synthesized by the methods described in the literature cited above.

Furthermore, the compounds Ia in which A is a group —CSNH₂ are obtained, for example, if an appropriately substituted bithienyl cyanide II is reacted
a) either with hydrogen sulfide in the presence of a base or
b) with a thiocarboxylic acid III in the presence of an acid in a conventional manner (Helv. Chim. Acta, 1960, 1522 et seq.).

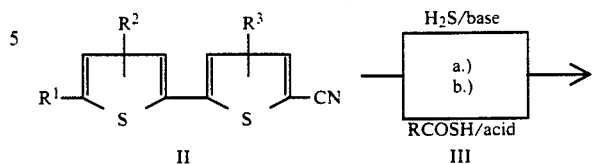

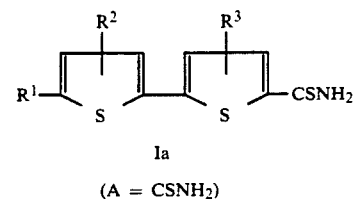

(A = CSNH₂)

The reaction according to route a.) is generally carried out in an inert organic solvent, such as methanol, ethanol, isopropanol, diethyl ether, tetrahydrofuran, ethyl acetate, methylene chloride, hexane, cyclohexane, tetralin or toluene or a mixture of these, at from −15° to 50° C., preferably from 10° to 35° C.

Particularly suitable bases are tertiary amines, such as triethylamine, dimethylphenylamine, N-methylpiperidine, N-methylmorpholine and pyridine. Particularly preferably, II and hydrogen sulfide are reacted in the presence of pyridine and/or triethylamine.

The reaction of II with a thiocarboxylic acid III in which R is a lower alkyl group, such as methyl, ethyl or 1-methylethyl, by route b.) is carried out similarly to known methods (The Chemistry of Amides; Interscience Publishers, New York 1970, page 417 et seq.), preferably in a lower carboxylic acid, such as acetic acid or propionic acid, as a solvent and in the presence or absence of water, at from 40° to 160° C., preferably from 70° to 130° C.

Compounds Ia, in which A is oxazol-2-yl or thiazol-2-yl are obtained, for example, by reacting an appropriate bithienyl carboxamide IVa or -thiocarboxamide Ia in a conventional manner (Bull. Soc. Chim. Fr., 1974, page 2079 et seq.) in an inert organic solvent with an α-halocarbonyl compound V or the corresponding acetal or ketal.

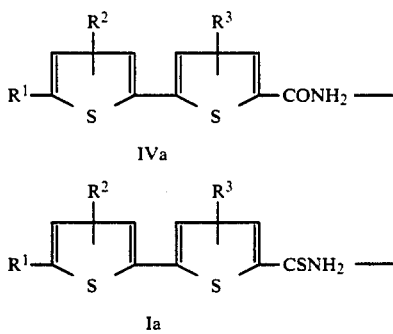

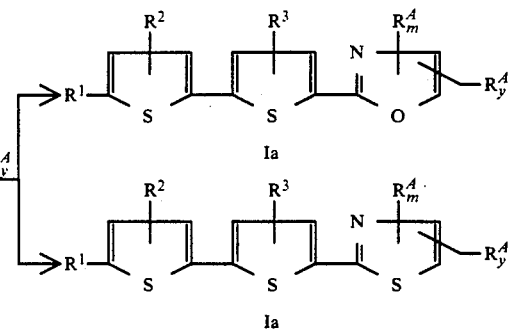

In formula V, Hal is halogen, such as fluorine, chlorine, bromine or iodine, preferably chlorine or bromine, $R^A$ is any substituent of the radical A as defined at the outset, and a plurality of these substituents in one molecule need not have the same meaning, n is 1 or 2 with n+m=2, and x is 0 or 1 with x+y=1.

Suitable solvents for this reaction are, in particular, polar inert organic solvents, such as methanol, ethanol, isopropanol, dimethylformamide, acetone, tert-butyl methyl ketone and acetonitrile.

The reaction temperature is in general from 40° to 170° C., preferably from 60° to 120° C.

It may also be advantageous, in order to increase the space-time yield of the reaction mixture, to add a base, such as the abovementioned tertiary amines and in particular piperidine, and/or to carry out the reaction at superatmospheric pressure (from 1 to 30, preferably from 1 to 5, atm).

Compounds Ia in which A is oxazol-5-yl are obtained by reacting an appropriate bithienylaldehyde derivative VI with an appropriate isonitrile VIIa or VIIb in a conventional manner (J. Org. Chem. 42 (1977), 3114 et seq.) in a polar organic solvent in the presence of a base.

Compounds Ia in which A is isoxazol-3-yl are obtained in a conventional manner (Houben-Weyl, Vol. 10/3, page 85 et seq.), by reacting a bithienyl nitrile oxide VIII with acetylene or an appropriately substituted alkyne IXa or IXb in an inert organic solvent.

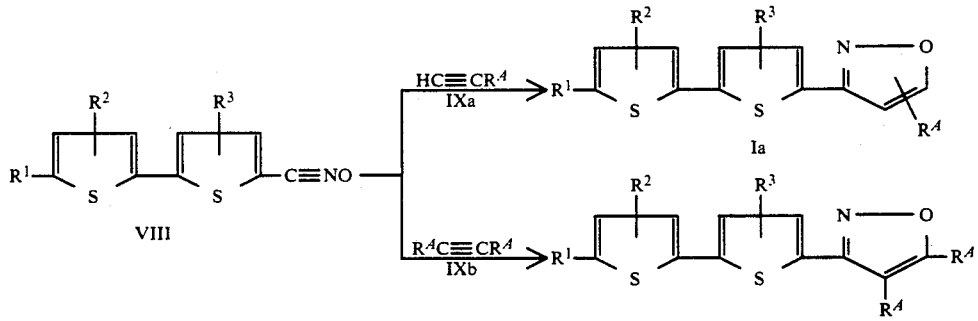

In formulae IXa and IXb, $R^4$ has the meaning stated above for compound V. Within the scope of this definition, the radicals $R^4$ in different positions (formula IXb and the corresponding reaction product) may have different meanings.

Aprotic organic solvents, such as methylene chloride, chloroform, carbon tetrachloride, chlorobenzene, toluene, xylene, cyclohexane, diethyl ether, dioxane and tetrahydrofuran, are preferably used for this reaction.

The reaction temperature is in general from −15° to 70° C., preferably from 10° to 40° C.

The bithienyl nitrile oxides VIII required for the reaction are obtained, for example according to DE-

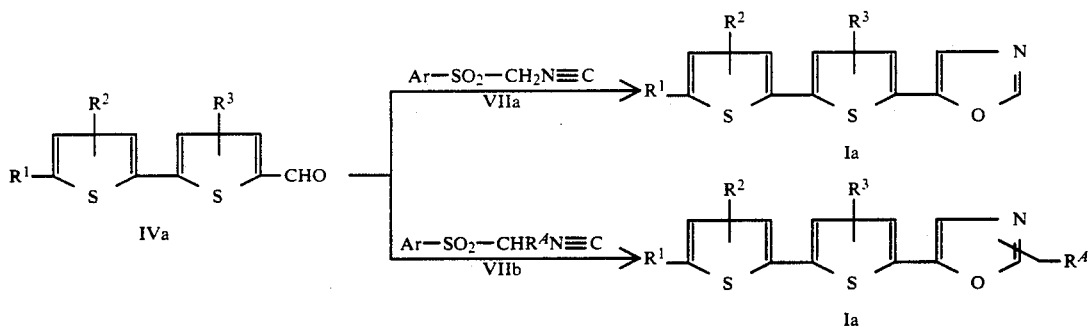

In formulae VIIa and VIIb, Ar is aryl, in particular phenyl or tolyl, and $R^4$ has the meaning stated above for compound V.

These reactions are carried out, in particular, in methanol, ethanol, isopropanol, dimethylformamide, acetone and/or acetonitrile as solvents, in the presence of an organic or inorganic base, such as the above-mentioned amines and methylates, ethylates, tert-butylates, hydroxides, carbonates and bicarbonates of alkali metal or alkaline earth metal cations, at from 30° to 150° C., preferably from 50° to 100° C.

A27 54 832, from the corresponding oximes of the aldehydes VI. As in the previous literature cited, the bithienyl nitrile oxides VIII are reacted, without prior isolation, i.e. in situ, with the acetylenes.

Compounds Ia in which A is pyrazol-5-yl are obtained in a conventional manner (The Chemistry of Heterocyclic Compounds—Pyrazoles etc., John Wiley and Sons, New York 1967, page 10 et seq.), by reacting a bithienyldicarbonyl derivative X with hydrazine or with a hydrazine derivative XI.

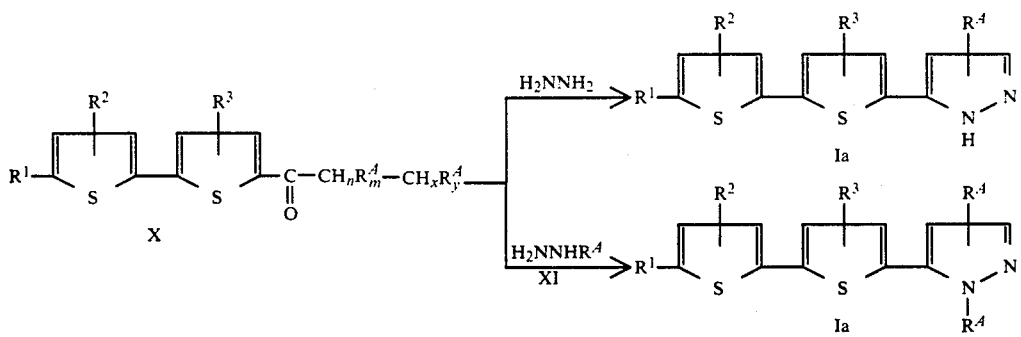

In formulae X and XI and their reaction product Ia, n, m, x, y and $R^A$ have the meanings stated for formula V. Within the scope of their definition, the radicals $R^A$ in different positions of a molecule may have different meanings.

Particularly suitable solvents for this reaction are the abovementioned protic polar solvents, in particular methanol, ethanol, acetic acid and/or propionic acid.

The reaction temperature is from 50° to 150° C., preferably from 80° to 120° C.

The bithienyldicarbonyl compounds X required for the reaction are obtained by known methods, for example by reacting an appropriate bithienylacyl compound XIIa or XIIb with the acetal or ketal of an N,N-dialkylcarboxamide XIIIa or XIIIb (U.S. Pat. No. 3,086,854; Adv. Org. Chem. 9 (1979), 393 et seq.).

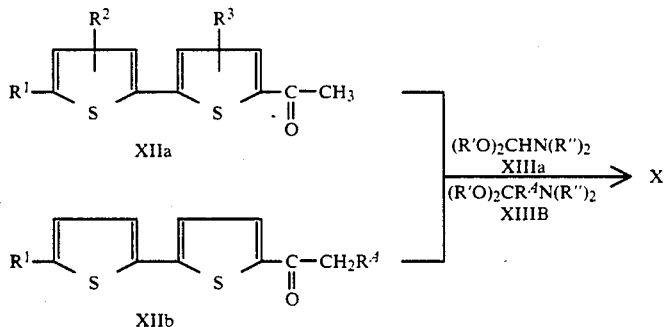

In formulae XIIIa and XIIIb, R' and R" are each $C_1$–$C_4$-alkyl, in particular methyl, ethyl or isopropyl.

For the synthesis of the novel substances or of the substances which can be used according to the invention, methods which are described in the publications below are also useful: Heterocycles 10 (1978), 57; Khim. Farm. ZH. 7(8) (1973), 13–17; Khim. Farm. ZH. 6(6) (1972), 24–28; Helv. Chim. Acta, (1960), 1522; Khim. Geterosikl. Soedin, (1972), 770–772; U.S. Pat. No. 3,268,543; GB 1 268 817; Synthesis Commun., (1987), 51; Inorg. Chim. Acta 125 (1986), 203–206; Bull. Chem. Soc. Jap. 58 (1985), 2126; J. Chem. Soc. Perkin II, (1972), 27; Heterocycles 18 (1982), 117; Tetrahedron 38(22) (1982), 3347; J. Org. Chem. 47(8) (1982), 1590 and Bull. Soc. Chim. Fr. (1974), 2079.

With regard to the biological activity as herbicides, particularly preferred compounds I are those in which $R^1$ and $R^2$ are each hydrogen; nitro; formyl; phenylcarbonyl;

halogen, such as fluorine, chlorine, bromine or iodine, preferably chlorine or bromine;

alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, preferably trifluoromethyl, cycloalkyl, such as cyclopropyl, cyclobutyl, cyclopentyl, cyclohexyl, cycloheptyl or cyclooctyl, preferably cyclopropyl, cyclopentyl or cyclohexyl;

cycloalkoxy, such as cyclopropoxy, cyclobutoxy, cyclopentyloxy, cyclohexyloxy, cycloheptyloxy or cyclooctyloxy, preferably cyclopropoxy, cyclopentyloxy or cyclohexyloxy;

alkoxy, such as methoxy, ethoxy, propoxy, 1-methylethoxy, butoxy, 1-methylpropoxy, 2-methylpropoxy or 1,1-dimethylethoxy, preferably methoxy, ethoxy or propoxy;

haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, preferably trifluoromethoxy;

alkylthio, such as methylthio, ethylthio, propylthio, 1-methylethylthio, butylthio, 1-methylpropylthio, 2-methylpropylthio or 1,1-dimethylethylthio, preferably methylthio or ethylthio;

haloalkylthio, such as difluoromethylthio, trifluoromethylthio, chlorodifluoromethylthio, dichlorofluoromethylthio, 2-fluoroethylthio, 2,2-difluoroethylthio, 1,1,2,2-tetrafluoroethylthio, 2,2,2-trifluoroethylthio or pentafluoroethylthio, preferably difluoromethylthio, trifluoromethylthio or pentafluoroethylthio;

alkylcarbonyl, such as acetyl, propionyl, isopropionyl, butyryl, 2-methylpropionyl, pentanoyl, 2-methylbutyryl, 3-methylbutyryl, 2,2-dimethylpropionyl, hexanoyl, 2-methylpentanoyl, 3-methylpentanoyl, 4-methylpentanoyl, 2,2-dimethylbutyryl, 2,3-dimethylbutyryl, 3,3-dimethylbutyryl or 2-ethylbutyryl, preferably acetyl, propionyl, butyryl and pentanoyl, which may be monosubstituted to trisubstituted by the above-mentioned halogen atoms, in particular fluorine, chlorine and/or bromine;

cycloalkylcarbonyl, such as cyclopropylcarbonyl, cyclobutylcarbonyl, cyclopentylcarbonyl or cyclohexylcarbonyl, preferably cyclopentylcarbonyl or cyclohexylcarbonyl, which may be monosubstituted to trisubstituted by halogen as stated above, in particular fluorine and/or chlorine, and/or alkyl as stated above and having one to four carbon atoms, in particular methyl, ethyl and/or 1-methylethyl, and alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl, preferably methoxycarbonyl or ethoxycarbonyl;

$R^3$ is hydrogen, halogen, alkyl, alkoxy, alkylthio, haloalkyl or haloalkoxy, each of one to four carbon atoms, as defined under $R^1$, preferably hydrogen, fluorine, chlorine, bromine, methyl, ethyl, propyl, butyl, methoxy, ethoxy, methylthio, difluoromethyl, trifluoromethyl, difluoromethoxy or trifluoromethoxy;

B is —CSNH$_2$;

pyridyl or quinolinyl, which may carry one to three of the groups stated in general and in particular for $R^3$;

phenyl or naphthyl, which may carry one to three of the following substituents: the groups stated for $R^3$, nitro, cyano, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-diemthyl-2-propenyl, 1,2-dimethyl-1-propenyl, 1,2-diemthyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-diemthyl-3-butenyl, 1,2-diemthyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, preferably ethenyl or 1-propenyl, and/or alkynyl, such as ethynyl, 1-propynyl, 2-propynyl, 1-butynyl, 2-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl or 1-ethyl-1-methyl-2-propynyl, preferably ethynyl or 1-propynyl; furyl, pyrrolyl, pyrazolyl, imidazolyl, oxazolyl, isoxazolyl, thiazolyl or a corresponding benzofused ring, such as indolyl, isoindolyl, benzofuranyl, benzopyrazolyl, benzimidazolyl, benzoxazolyl, benzisoxazolyl or benzothiazolyl, and these ring systems may carry one to five halogen atoms as stated for $R^1$, in particular fluorine and/or chlorine and/or one to three of the following radicals:

alkyl, alkoxy and/or alkylthio, in particular as stated for $R^3$, which may in turn be monosubstituted to pentasubstituted by, in particular, fluorine and/or chlorine and/or monosubstituted by alkoxy, in particular methoxy or ethoxy, haloalkoxy, in particular difluoromethoxy or trifluoromethoxy, alkylthio, in particular methylthio or ethylthio, amino, alkylamino, in particular methylamino or ethylamino, or dialkylamino, such as dimethylamino or diethylamino, cycloalkyl of three to six carbon atoms, as stated in particular for $R^3$, and/or phenyl, which may in turn carry one to five halogen atoms, in particular fluorine or chlorine, and/or one to three of the radicals stated in particular for $R^3$, and a radical —NR$^4$R$^5$ or a radical —COR$^6$;

$R^4$ and $R^5$ are each hydrogen; formyl;

alkyl as stated for $R^1$, in particular methyl, ethyl and/or 1-methylethyl;

haloalkyl as stated in general and in particular for $R^1$;

alkoxy as stated in general and in particular for $R^3$;

haloalkoxy as stated for $R^3$, in particular difluoromethoxy or trifluoromethoxy;

alkylcarbonyl as stated in general and in particular for $R^1$, which may carry one to three halogen atoms, in particular fluorine and/or chlorine, in the alkyl moiety, and alkoxycarbonyl as stated for $R^1$, in particular methoxycarbonyl, ethoxycarbonyl, 1-methylethoxycarbonyl or 1,1-dimethylethoxycarbonyl, and/or phenylcarbonyl which in turn may carry one to five halogen atoms, in particular fluorine or chlorine, and/or one to three of the following groups: alkyl, in particular methyl or ethyl, haloalkyl, in particular difluoromethyl or trifluoromethyl, alkoxy, in particular methoxy or 1-methylethoxy and/or haloalkoxy, in particular difluoromethoxy or trifluoromethoxy;

$R^6$ is hydroxyl;

alkoxy as stated for $R^1$, in particular methoxy, ethoxy or 1-methylethoxy;

alkoxyalkoxy, such as 2-methoxyethoxy, 2-ethoxyethoxy, 2-methoxypropoxy, 3-methoxypropoxy, 2-ethoxypropoxy, 3-ethoxypropoxy, 1-methyl-2-methoxyethoxy, 2-ethoxy-1-methylethoxy, 2-methoxy-1-methylpropoxy, 2-ethoxy-1-methylpropoxy or 2-methoxy-2-methylpropoxy, in particular 2-methoxyethoxy, 2-ethoxyethoxy, 2-methoxypropoxy or 2-methoxy-1-methylethoxy;

alkenyloxy, such as allyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1,2-dimethyl-2-propenyloxy, 1,1-dimethyl-2-propenyloxy, 1-methyl-3-butenyloxy, 1-ethyl-2-propenyloxy, 2-hexenyloxy, 1-methyl-2-pentenyloxy, 1-ethyl-2-butenyloxy or 2-ethyl-2-butenyloxy, preferably allyloxy, 2-butenyloxy or 3-butenyloxy;

alkynyloxy, such as 2-propynyloxy, 2-butynyloxy, 3-butynyloxy, 1-methyl-2-propynyloxy, 1-methyl-2-butynyloxy, 1-ethyl-2-propynyloxy, 2-pentynyloxy, 3-pentynyloxy, 4-pentynyloxy or 1-methyl-2-pentynyloxy, preferably 2-propynyloxy;

phenoxy or benzyloxy, where the aromatic rings may in turn be monosubstituted to pentasubstituted by halogen as stated above for $R^1$, in particular fluorine or chlorine, and/or monosubstituted to trisubstituted by alkyl, haloalkyl, alkoxy or haloalkoxy as stated for $R^1$, in particular of one or two carbon atoms;

or a group $NR^7R^8$, and $R^7$ and $R^8$ are each hydrogen;

alkyl as stated in general and in particular for $R^1$;

alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl or 3-butenyl;

alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl;

alkoxyalkyl, such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl or 1-ethoxy-1-methylethyl, in particular methoxyethyl or ethoxyethyl, or phenyl or benzyl.

The bithienyl derivatives I, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. The active ingredients are used in a purity of from 90 to 100, and preferably from 95 to 100, % (according to the NMR spectrum).

The compounds I according to the invention may be formulated for example as follows.

I. 90 parts by weight of compound no. 1.002 is mixed with 10 parts by weight of N-methyl-alpha-pyrrolidone. A mixture is obtained which is suitable for application in the form of very fine drops.

II. 20 parts by weight of compound no. 2.001 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 6.006 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 7.001 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 8.001 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 10.002 is intimately mixed with 97 parts by weight of particulate kaolin. A dust is obtained containing 3% by weight of the active ingredient.

VII. 30 parts by weight of compound no. 11.010 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 13.005 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 1.0, kg of active ingredient per hectare. In view of the number of application methods possible, the compounds according to the invention, or agents containing them, may be used in a further large number of crops for removing unwanted plants. The following crops are given by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |

-continued

| Botanical name | Common name |
| --- | --- |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum (Gossypium arboreum, Gossypium herbaceum, Gossypium vitifolium)* | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum (N. rustica)* | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor (s. vulgare)* | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the bithienyl derivatives I may be mixed and applied together with numerous representatives of other herbicidal or growth-regulating active ingredient groups. Examples of suitable components are diazines, 4H-3,1-benzoxazine derivatives, benzothiadiazionones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, aryloxy- or heteroaryloxyphenylpropionic acids and salts, esters and amides thereof, etc.

It may also be useful to apply the herbicidal compounds I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were used, after appropriate modifications of the starting materials, to obtain further compounds I. The compounds thus obtained, or obtained in accordance with the literature cited above (WO-A 86/05949), are listed with physical data in the tables below. Compounds without these data may be obtained analogously. In view of their close structural relationship, they are expected to have a similar action.

EXAMPLE 1

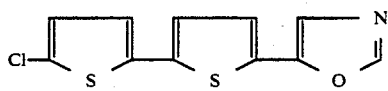

20 mmol of 5'-chlorobithienyl-5-carbaldehyde and 20 mmol of p-toluenesulfonylmethyl isocyanite were dispersed in 60 ml of methanol and 40 mmol of potassium carbonate was added, at 20° C., to the mixture thus obtained. The reaction mixture was refluxed for 30 minutes. The addition of water to the cold reaction mixture gave the desired product as a solid.

(Yield: 60%; mp. 89° C.; compound no. 1.002).

EXAMPLE 2

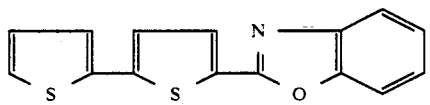

46 mmol of bithienyl-5-carbaldehyde, 46 mmol of o-aminophenol and 45 ml of ethanol were stirred for 4 hours at 80° C. After the mixture had cooled, the hydroxyimino compound was obtained as a solid in a yield of 88%.

5 g of this intermediate was stirred with 4.8 g of silver oxide and 20 ml of methylene chloride for 10 hours at 20° C. The reaction mixture was freed from inorganic impurities and concentrated under reduced pressure, and the product thus obtained was purified by chromatography.

(Yield: 50%; mp. 129°–131° C; Compound no. 14.001).

EXAMPLE 3

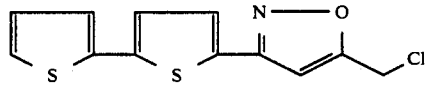

At 0° C., 5.0 g of propargyl chloride and then 31.5 g of 10% strength sodium hypochlorite solution (in water) and 0.5 g of sodium hydroxide were added to a mixture of 8.1 g of bithienyl-5-carbaldoxime and 50 ml of methylene chloride, and the reaction mixture was kept at 20° C. for 10 hours. The product was isolated by working up the organic phase in conventional manner, followed by chromatography.

(Yield: 6.9 g; mp. 80° C.; compound no. 2.002).

EXAMPLE 4

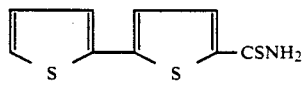

At −5° C., 300 ml of ice and then 35 g of hydroxylamine-O-sulfate were added to a solution of 47.5 g of bithienyl-5-carbaldehyde, 400 ml of ether and 30 ml of methylene chloride. After the mixture had been stirred for one hour at −5° C., the organic solvent was removed, with cooling, under reduced pressure. The aqueous phase was purified with the aid of activated carbon and then stirred at 0° C. into 250 ml of 4N caustic soda solution, whereupon bithienyl-5-cyanide precipitated out.

20 g of the cyanide thus obtained, 4 ml of glacial acetic acid and 44 g of thioacetic acid were stirred for 30 minutes at 75° C. The product was isolated from the reaction mixture by stirring in 250 ml of a 1:1 mixture of isopropanol and water.

(Yield: 15.1 g; mp. >200° C.; Compound no. 7.001).

A mixture of 3.0 g of α-bromoacetophenone, 3.0 g of bithienyl-5-thioamide (Example 4), 2 drops of piperidine and 50 ml of isopropanol was refluxed for 30 minutes. When the reaction mixture cooled the product precipitated as a solid.

(Yield: 2.95 g; mp. 139°–141° C.; Compound no. 6.007).

EXAMPLE 6

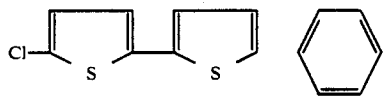

a) In 140 ml of ether, 17.4 g (0.725 mol) of magnesium shavings was reacted according to Grignard with 118 g (0.723 mol) of 2-bromothiophene, and this solution was then introduced into 280 ml of ether, 1.5 g (2.8 mmol) of 1,3-bis(diphenylphosphino)propane nickel dichloride and 140 g (0.586 mol) of 5-bromo-2-phenylthiophene. After the slightly exothermic reaction had subsided, the mixture was stirred for 4 hours at boiling point, and the solution thus obtained was then diluted with 280 ml of ether and stirred into 280 ml of 2N hydrochloric acid solution. The crystals which precipitated out were isolated and dried. There was obtained 98.4 g (69.4% of theory) of 5-phenyl-[2,2'-bithienyl], mp. 116.5°–118° C.

A further 37.5 g of a solid consisting to the extent of 71% of 5-phenyl-[2,2'-bithienyl] (HPLC analysis) was obtained from the mother liquor after washing, drying, concentration and recrystallization from isopropanol with a little activated carbon.

b) At 42° C. and within a period of 2 minutes, 2.4 g (17.8 mmol) of sulfuryl chloride was added to 30 ml of glacial acetic acid, 0.1 g (0.75 mmol) of aluminum trichloride and 3.5 g (14 mmol) of compound a), and the mixture obtained was stirred for 4 hours at 50° C. The precipitate was isolated, washed with water and dried. There was obtained 2.2 g (56.8% of theory) of 5'-chloro-5-phenyl-[2,2'-bithienyl], mp: 128°–132° C.; Compound no. 17.003.

TABLE 1

I.1

Structure: R¹-thiophene(R²)-thiophene(R³)-oxazoline with X¹, X²

| No. | R¹ | R² | R³ | X¹ | X² | Phys. data |
|---|---|---|---|---|---|---|
| 1.002 | H | H | H | H | H | mp. 80–81° C. |
| 1.002 | Cl | H | H | H | H | mp. 89° C. |
| 1.003 | H | H | H | H | $CH_3$ | |
| 1.004 | H | H | H | H | $CH_2CH_3$ | |
| 1.005 | Cl | H | H | H | $CH_3$ | |
| 1.006 | H | H | H | $CH_3$ | H | |
| 1.007 | Cl | H | H | H | H | |
| 1.008 | $CH_2CH_3$ | H | H | H | H | |
| 1.009 | Cl | H | H | H | $CH_3$ | |
| 1.010 | Br | H | H | H | H | |
| 1.011 | H | H | H | H | $C_6H_5$ | |
| 1.012 | Cl | H | H | H | H | |
| 1.013 | $CH_3$ | 4'-$CH_3$ | H | H | H | |
| 1.014 | $CH_3$ | 4'-$CH_3$ | H | H | $CH_3$ | |
| 1.015 | H | H | 4-$CH_3$ | H | H | |
| 1.016 | $COOCH_3$ | H | H | H | H | |
| 1.017 | COOH | H | H | H | H | |
| 1.018 | $COOCH_2CH_3$ | H | H | H | H | |
| 1.019 | H | H | H | H | $CF_3$ | |
| 1.020 | H | H | H | $CH_2CH_3$ | H | |
| 1.021 | H | H | H | H | 4-Cl—$C_6H_4$ | |

TABLE 2

I.2

| No. | R¹ | R² | R³ | X¹ | X² | Phys. data |
|---|---|---|---|---|---|---|
| 2.001 | H | H | H | H | H | mp. 93–95° C. |
| 2.002 | H | H | H | H | $CH_2Cl$ | mp. 80° C. |
| 2.003 | Cl | H | H | H | H | |
| 2.004 | Br | H | H | H | H | |
| 2.005 | Cl | H | H | H | $CH_2Cl$ | |
| 2.006 | Br | H | H | H | $CH_2Cl$ | |
| 2.007 | H | H | H | H | $COOCH_2CH_3$ | |
| 2.008 | H | H | H | H | $COOCH_3$ | |
| 2.009 | H | H | H | H | $C_6H_5$ | |
| 2.010 | H | H | H | $CH_3$ | H | |
| 2.011 | $CH_3$ | H | H | H | H | |
| 2.012 | $CH_2CH_3$ | H | H | H | H | |
| 2.013 | $CH_3$ | H | H | H | $CH_2Cl$ | |
| 2.014 | H | H | 4-$CH_3$ | H | H | |
| 2.015 | H | H | 4-$CH_2CH_3$ | H | H | |
| 2.016 | $CH_3$ | H | 4-$CH_3$ | H | H | |
| 2.017 | COOH | H | H | H | H | |
| 2.018 | $COOCH_3$ | H | H | H | H | |
| 2.019 | $COOCH_2CH_3$ | H | H | H | H | |
| 2.020 | $CONH_2$ | H | H | H | H | |
| 2.021 | H | H | H | H | $CH_2OH$ | |

TABLE 3

I.3

| No. | R¹ | R² | R³ | X³ | X¹ | X² | Phys. data |
|---|---|---|---|---|---|---|---|
| 3.001 | H | H | H | $C_6H_5$ | H | H | |
| 3.002 | H | H | H | 4-Cl—$C_6H_4$ | H | H | |
| 3.003 | H | H | H | 4-F—$C_6H_4$ | H | H | |
| 3.004 | H | H | H | 4-$CH_3$—$C_6H_4$ | H | H | |

TABLE 3-continued

I.3

Structure: R¹-S(4',3')-R²-S(4,3)-R³ ring with pyrazole bearing X¹, X², X³ (N-X³)

| No. | R¹ | R² | R³ | X³ | X¹ | X² | Phys. data |
|---|---|---|---|---|---|---|---|
| 3.005 | H | H | H | (furan-2-yl, O) | H | H | |
| 3.006 | H | H | H | (pyridin-2-yl, N) | H | H | |
| 3.007 | H | H | H | H | CH₃ | H | |
| 3.008 | H | H | H | H | H | CH₃ | |
| 3.009 | H | H | H | H | H | C₆H₅ | |
| 3.010 | Cl | H | H | H | H | C₆H₅ | |
| 3.011 | CH₃ | H | H | H | H | H | |
| 3.012 | CH₂CH₃ | H | H | H | H | H | |
| 3.013 | Br | H | H | H | H | H | |
| 3.014 | Cl | H | H | H | CH₃ | CH₃ | |
| 3.015 | Cl | H | H | C₆H₅ | CH₃ | CH₃ | |
| 3.016 | H | H | 4-CH₃ | CH₃ | H | H | |
| 3.017 | Cl | H | H | CH₃ | H | H | |
| 3.018 | CH₃ | H | H | CH₃ | H | H | |
| 3.019 | CH₃ | H | H | C₆H₅ | CH₃ | CH₃ | |
| 3.020 | OCH₃ | H | H | CH₃ | H | H | |

TABLE 4

| No. | R¹ | R² | R³ | X³ | X¹ | X² | Phys. data |
|---|---|---|---|---|---|---|---|
| 4.001 | H | H | H | C₆H₅ | H | H | |
| 4.002 | H | H | H | 4-Cl—C₆H₄ | H | H | |
| 4.003 | H | H | H | 4-F—C₆H₄ | H | H | |
| 4.004 | H | H | H | 4-CH₃—C₆H₄ | H | H | |
| 4.005 | H | H | H | (furan-2-yl, O) | H | H | |
| 4.006 | H | H | H | (pyridin-2-yl, N) | H | H | |
| 4.007 | H | H | H | H | CH₃ | H | |
| 4.008 | H | H | H | H | H | CH₃ | |
| 4.009 | H | H | H | H | CH₃ | CH₃ | |
| 4.010 | Cl | H | H | H | H | H | |
| 4.011 | CH₃ | H | H | H | H | H | |
| 4.012 | CH₂CH₃ | H | H | H | H | H | |
| 4.013 | Br | H | H | H | H | H | |
| 4.014 | Cl | H | H | H | CH₃ | CH₃ | |
| 4.015 | Cl | H | H | C₆H₅ | CH₃ | CH₃ | |
| 4.016 | H | 4'-CH₃ | H | CH₃ | H | CH₃ | |
| 4.017 | Cl | H | H | CH₃ | H | H | |
| 4.018 | Cl | H | H | CH₃ | H | CH₃ | |
| 4.019 | CH₃ | H | H | C₆H₅ | CH₃ | CH₃ | |
| 4.020 | OCH₃ | H | H | H | H | H | |
| 4.021 | CH₃ | H | 4-CH₃ | H | H | H | |

TABLE 5

I.5

| No. | R¹ | R² | R³ | X¹ | X² | Phys. data |
|---|---|---|---|---|---|---|
| 5.001 | H | H | H | H | H | |
| 5.002 | H | H | H | CH₃ | H | |
| 5.003 | H | H | H | H | CH₃ | |
| 5.004 | CH₃ | H | H | H | CH₃ | |
| 5.005 | H | H | 4-CH₃ | H | H | |
| 5.006 | H | 4'-CH₃ | H | H | H | |
| 5.007 | Cl | H | H | H | CH₃ | |
| 5.008 | CH₂CH₃ | H | H | H | CH₃ | |
| 5.009 | Br | H | H | H | CH₃ | |
| 5.010 | H | H | H | C₆H₅ | H | |
| 5.011 | Cl | H | 4-Cl | H | CH₃ | |
| 5.012 | OCH₃ | H | H | CH₃ | CH₃ | |
| 5.013 | Cl | H | H | CH₃ | CH₃ | |
| 5.014 | Cl | H | H | CH₃ | CH₃ | |
| 5.015 | Cl | 4'-CH₃ | H | CH₃ | CH₃ | |
| 5.016 | H | H | H | CH₂CH₃ | CH₂CH₃ | |
| 5.017 | H | H | H | H | CH₂C₆H₅ | |
| 5.018 | H | H | H | CH₂CH₃ | H | |
| 5.019 | H | H | H | CH₂OCH₃ | H | |
| 5.020 | Cl | H | H | CH₂OCH₃ | H | |

TABLE 6

Structure I.6: thiophene-thiophene-thiophene with N=C(X¹)(X²), substituents R¹, R², R³

| No. | R¹ | R² | R³ | X¹ | X² | Phys. data |
|---|---|---|---|---|---|---|
| 6.001 | H | H | H | H | H | |
| 6.002 | H | H | H | H | CH₃ | |
| 6.003 | Cl | H | H | H | C(CH₃)₃ | |
| 6.004 | Cl | H | H | H | C₆H₅ | |
| 6.005 | H | H | H | H | COOCH₂CH₃ | mp. 86–88° C. |
| 6.006 | H | H | H | H | 4-F—C₆H₄ | mp. 155–157° C. |
| 6.007 | H | H | H | H | C₆H₅ | mp. 139–141° C. |
| 6.008 | H | H | H | H | C(CH₃)₃ | mp. 81–83° C. |
| 6.009 | H | H | H | CH₃ | C₆H₅ | mp. 106–108° C. |
| 6.010 | Br | H | H | H | H | |
| 6.011 | CH₃ | H | H | H | H | |
| 6.012 | CH₃ | H | H | H | C₆H₅ | |
| 6.013 | H | 4'-CH₃ | H | H | C₆H₅ | |
| 6.014 | Cl | H | 4-Cl | H | H | |
| 6.015 | Cl | H | 4-Cl | H | C₆H₅ | |
| 6.016 | CH₃ | H | 4-CH₃ | H | H | |
| 6.017 | CH₃ | H | 4-CH₃ | H | C₆H₅ | |
| 6.018 | H | H | H | H | CH₃ | |
| 6.019 | H | H | H | H | CH₂Cl | |
| 6.020 | Cl | H | H | H | CH₂Cl | |
| 6.021 | CH₃ | H | H | H | CH₂Cl | |
| 6.022 | OCH₃ | H | H | H | C₆H₅ | |

TABLE 7

Structure I.7: thiophene-thiophene-thiophene-CSNH₂, substituents R¹, R², R³

| No. | R¹ | R² | R³ | Phys. data |
|---|---|---|---|---|
| 7.001 | H | H | H | mp. >200° C. |
| 7.002 | CH₃ | H | H | |
| 7.003 | CH₂CH₃ | H | H | |
| 7.004 | cyclopropyl | H | H | |
| 7.005 | OCH₃ | H | H | |
| 7.006 | OCH₂CH₃ | H | H | |
| 7.007 | Cl | H | 4-Cl | |
| 7.008 | Cl | H | H | mp. >200° C. |
| 7.009 | H | 4'-CH₃ | H | |
| 7.010 | Cl | 4'-CH₃ | H | |
| 7.011 | H | H | 4-CH₃ | |
| 7.012 | Br | H | H | |
| 7.013 | COOCH₃ | H | H | |
| 7.014 | Cl | 4'-Cl | 4-Cl | |
| 7.015 | COOCH₃ | H | H | |
| 7.016 | COOCH₂CH₃ | H | H | |

TABLE 8

Structure I.8: thiophene-thiophene-furan with X¹, X², X³ substituents on furan ring

| No. | R¹ | R² | R³ | X¹ | X² | X³ | Phys. data |
|---|---|---|---|---|---|---|---|
| 8.001 | H | H | H | H | H | H | mp. 83° C. |
| 8.002 | CH₃ | 4'-CH₃ | H | H | H | H | |
| 8.003 | Cl | H | H | H | H | H | |
| 8.004 | Br | H | H | H | H | H | |
| 8.005 | OCH₃ | H | H | H | H | H | |
| 8.006 | CH₃ | H | 4-CH₃ | H | H | H | |
| 8.007 | H | H | H | H | H | CH₃ | |
| 8.008 | H | H | H | H | CH₃ | H | |
| 8.009 | CH₃ | H | H | H | H | CH₂Cl | |
| 8.010 | CH₃ | H | H | H | H | CH₂OH | |
| 8.011 | CH₃ | 4'-CH₃ | H | H | H | H | |
| 8.012 | H | H | H | H | H | CH(OCH₃)₂ | |
| 8.013 | CH₃ | H | H | H | H | CH₂OCH₃ | |
| 8.014 | H | H | H | H | H | CH=N—OCH₃ | |
| 8.015 | CH₃ | H | H | H | H | CH=N—OCH₃ | |
| 8.016 | H | H | H | H | H | CH=N—OCH₂CH₃ | |
| 8.017 | CH₃ | H | H | H | H | CH=N—OCH₂CH₃ | |
| 8.018 | CN | H | H | H | H | H | |
| 8.019 | H | H | H | CH₃ | H | H | |
| 8.020 | H | H | H | H | CH₂OCH₃ | H | |

TABLE 9

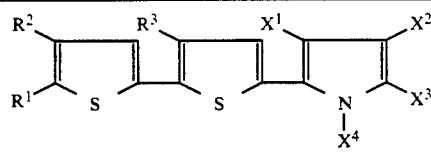

| No. | R¹ | R² | R³ | X¹ | X² | X³ | X⁴ | Phys. data |
|---|---|---|---|---|---|---|---|---|
| 9.001 | H | H | H | H | H | H | $CH_3$ | mp. 47–48° C. |
| 9.002 | H | H | H | H | H | H | $CH_2CH_3$ | |
| 9.003 | Cl | H | H | H | H | H | H | |
| 9.004 | $CH_3$ | H | H | H | H | H | H | |
| 9.005 | Br | H | H | H | H | H | H | |
| 9.006 | $OCH_3$ | H | H | H | H | H | H | |
| 9.007 | Cl | H | H | H | H | H | $CH_3$ | |
| 9.008 | $CH_3$ | H | H | H | H | H | $CH_3$ | |
| 9.009 | Br | H | H | H | H | H | $CH_3$ | |
| 9.010 | $CH_3$ | H | H | H | H | H | $CH_3$ | |
| 9.011 | H | H | H | H | H | $CH_3$ | $CH_3$ | |
| 9.012 | H | H | H | H | H | $CH_2CH_3$ | $CH_3$ | |
| 9.013 | H | H | H | H | H | $C_6H_5$ | H | |
| 9.014 | $CH_3$ | H | H | H | H | $CH_3$ | H | |
| 9.015 | $CH_3$ | H | H | H | H | $CH_2CH_3$ | H | |
| 9.016 | $CH_2CH_3$ | H | H | H | H | H | $CH_3$ | |
| 9.017 | $(CH_2)_3CH_3$ | H | H | H | H | H | $CH_3$ | |
| 9.018 | $CH_3$ | H | H | $CH_3$ | $CH_3$ | H | H | |
| 9.019 | H | H | H | H | H | $COOCH_3$ | $CH_3$ | |
| 9.020 | H | H | H | H | H | $CH=N-OCH_3$ | H | |
| 9.021 | H | 4'-$CH_3$ | 4-$CH_3$ | H | H | H | $CH_3$ | |

TABLE 10

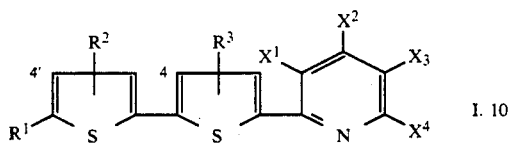

I. 10

| No. | R¹ | R² | R³ | X¹ | X² | X³ | X⁴ | Phys. data |
|---|---|---|---|---|---|---|---|---|
| 10.001 | H | H | H | H | H | H | H | mp. 120° C. |
| 10.002 | H | H | H | H | H | H | Cl | mp. 121° C. |
| 10.003 | $CH_3$ | H | H | H | H | H | H | |
| 10.004 | $CH_2CH_3$ | H | H | H | H | H | H | |
| 10.005 | $(CH_2)_2CH_3$ | H | H | H | H | H | H | |
| 10.006 | $OCH_3$ | H | H | H | H | H | H | |
| 10.007 | $CH_3$ | H | H | H | H | H | $CF_3$ | |
| 10.008 | $CH_3$ | H | H | H | H | H | Cl | |
| 10.009 | $CH_3$ | H | H | H | Cl | $CF_3$ | H | |
| 10.010 | $CH_3$ | H | H | H | H | H | F | |
| 10.011 | $CH_3$ | H | H | H | H | Cl | H | |
| 10.012 | $CH_3$ | H | H | H | $CF_3$ | H | H | |
| 10.013 | H | H | H | H | $CF_3$ | H | H | |
| 10.014 | $CH_3$ | 4'-$CH_3$ | H | H | H | H | H | |
| 10.015 | $CH_3$ | H | 4-$CH_3$ | H | H | H | H | |
| 10.016 | $CH_3$ | H | H | Cl | H | H | H | |
| 10.017 | $CH_2CH_3$ | H | H | H | $CF_3$ | H | H | |
| 10.018 | $CH_3$ | H | H | $CF_3$ | H | H | H | |
| 10.019 | H | H | H | $CF_3$ | H | H | H | |
| 10.020 | $OCH_3$ | H | H | $CF_3$ | H | H | H | |
| 10.021 | $OCH_3$ | H | H | H | $CF_3$ | H | H | |
| 10.022 | $CH_3$ | H | H | H | H | H | F | |
| 10.023 | $CH_2CH_3$ | H | H | H | H | H | F | |
| 10.024 | $CH_3$ | H | H | H | H | H | $CH_3$ | |
| 10.025 | $CH_3$ | 4'-$CH_3$ | H | H | $CF_3$ | H | H | |
| 10.026 | $CH_3$ | H | H | H | H | $CH_3$ | H | |
| 10.027 | H | H | H | $CF_3$ | H | Cl | H | |
| 10.028 | $CH_3$ | H | H | $CF_3$ | H | Cl | H | |
| 10.029 | $OCH_3$ | H | H | H | H | H | $CF_3$ | |
| 10.030 | $CH_2CH_3$ | H | H | H | H | H | $CF_3$ | |
| 10.031 | $(CH_2)_2CH_3$ | H | H | H | H | H | $CF_3$ | |

TABLE 11

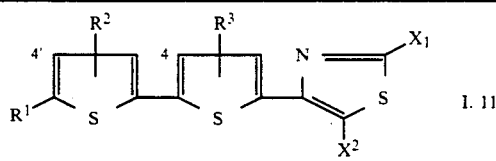

I. 11

| No. | R[1] | R[2] | R[3] | X[1] | X[2] | Phys. data |
|---|---|---|---|---|---|---|
| 11.001 | H | H | H | $CH_3$ | H | |
| 11.002 | H | H | H | $CH(CH_3)_2$ | H | |
| 11.003 | H | H | H | H | H | |
| 11.004 | $CH_3$ | H | H | $CH_3$ | H | |
| 11.005 | $CH_2CH_3$ | H | H | $CH_3$ | H | |
| 11.006 | Br | H | H | $CH_3$ | H | |
| 11.007 | Cl | H | H | $CH_3$ | H | |
| 11.008 | H | H | H | $NH_2$ | H | mp. 201–202° C. |
| 11.009 | Br | H | H | $NH_2$ | H | mp. 185–190° C. |
| 11.010 | Br | H | H | $NHCOCH_3$ | H | mp. 231–232° C. |
| 11.011 | $NO_2$ | H | H | $NH_2$ | H | mp. >240° C. |
| 11.012 | H | H | H | $C_6H_5$ | H | |
| 11.013 | H | H | H | $NHCH_3$ | H | |
| 11.014 | $CH_3$ | H | H | $NHCH_3$ | H | |
| 11.015 | $CH_2CH_3$ | H | H | $NHCH_3$ | H | |
| 11.016 | $CH_3$ | H | H | NHCHO | H | |
| 11.017 | $CH_3$ | H | H | $NHCOCH_2CH_3$ | H | |
| 11.018 | $CH_3$ | 4'-$CH_3$ | H | $NH_2$ | H | |
| 11.019 | $CH_3$ | 4'-$CH_3$ | 4-$CH_3$ | $CH_3$ | H | |
| 11.020 | $OCH_3$ | H | H | $CH_3$ | H | |
| 11.021 | $CH_3$ | H | H | 4-F—$C_6H_4$ | H | |

TABLE 12

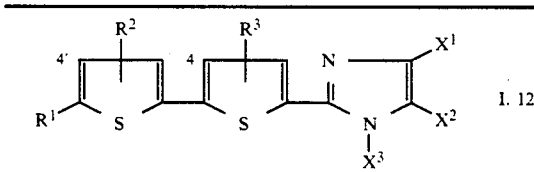

I. 12

| No. | R[1] | R[2] | R[3] | X[3] | X[1] | X[2] | Phys. data |
|---|---|---|---|---|---|---|---|
| 12.001 | H | H | H | $CH_3$ | H | H | |
| 12.002 | H | H | H | $CH_2CH_3$ | H | H | |
| 12.003 | H | H | H | $CH_3$ | H | $C_6H_5$ | |
| 12.004 | Cl | H | H | $CH_3$ | H | H | |
| 12.005 | Br | H | H | $CH_3$ | H | H | |
| 12.006 | $OCH_3$ | H | H | $CH_3$ | H | H | |
| 12.007 | Cl | H | H | H | H | H | |
| 12.008 | Br | H | H | H | H | H | |
| 12.009 | $OCH_3$ | H | H | H | H | H | |
| 12.010 | $CH_3$ | 4'-$CH_3$ | H | $CH_3$ | H | H | |

TABLE 13

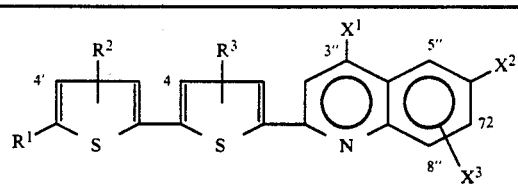

I. 13

| No. | R[1] | R[2] | R[3] | X[1] | X[2] | X[3] | Phys. data |
|---|---|---|---|---|---|---|---|
| 13.001 | H | H | H | $COOCH_2CH_3$ | H | H | mp. 96–97° C. |
| 13.002 | H | H | H | $CONHC_6H_5$ | H | H | mp. 309–310° C. |
| 13.003 | $CH_3$ | H | H | H | H | H | mp. 128–130° C. |
| 13.004 | $CH(OCH_3)_2$ | H | H | H | H | H | oil |
| 13.005 | H | H | H | $CH_3$ | H | H | mp. 145–148° C. |
| 13.006 | H | H | H | H | $OCH_3$ | H | mp. 177° C. |
| 13.007 | H | H | H | H | Cl | H | mp. 140° C. |
| 13.008 | $CH_3$ | 4'-$CH_3$ | H | H | H | H | |
| 13.009 | $CH_3$ | H | H | H | H | 7"-$CH_3$ | |
| 13.010 | $CH_2CH_3$ | H | H | H | H | H | |
| 13.011 | H | H | H | $CF_3$ | H | H | |
| 13.012 | $CH_3$ | H | H | $CF_3$ | H | H | |
| 13.013 | Br | H | H | H | H | H | |
| 13.014 | Cl | H | H | H | H | H | |
| 13.015 | $OCH_3$ | H | H | H | H | H | |
| 13.016 | $CH_3$ | H | 4-$CH_3$ | H | H | H | |
| 13.017 | $CH_3$ | H | H | H | Cl | H | |
| 13.018 | Br | H | H | $CF_3$ | H | H | |

TABLE 13-continued

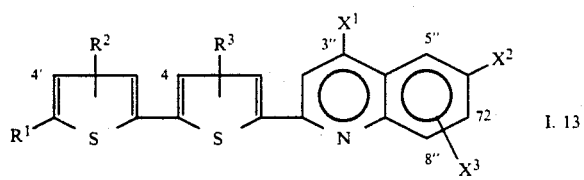

I. 13

| No. | R$^1$ | R$^2$ | R$^3$ | X$^1$ | X$^2$ | X$^3$ | Phys. data |
|---|---|---|---|---|---|---|---|
| 13.019 | OCH$_3$ | H | H | CF$_3$ | H | H | |
| 13.020 | H | H | H | H | H | H | |

TABLE 14

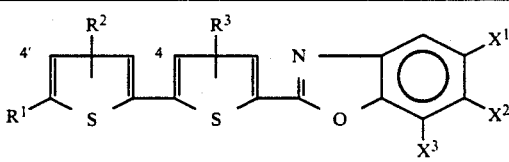

I.14

| No. | R$^1$ | R$^2$ | R$^3$ | X$^1$ | X$^2$ | X$^3$ | Phys. data |
|---|---|---|---|---|---|---|---|
| 14.001 | H | H | H | H | H | H | mp. 129–131° C. |
| 14.002 | Cl | H | H | H | H | H | |
| 14.003 | CH$_3$ | H | H | H | H | H | mp. 136° C. |
| 14.004 | CH$_2$CH$_3$ | H | H | H | H | H | |
| 14.005 | Br | H | H | H | H | H | |
| 14.006 | H | H | H | Cl | H | H | |
| 14.007 | H | H | H | Cl | H | Cl | |
| 14.008 | H | H | H | CH$_3$ | H | H | |
| 14.009 | H | H | H | C$_6$H$_5$ | H | H | |
| 14.010 | H | H | H | C(CH$_3$)$_3$ | H | H | |
| 14.011 | H | H | H | CH$_3$ | H | CH$_3$ | |
| 14.012 | H | H | H | NO$_2$ | H | H | |
| 14.013 | H | H | H | NHCOCH$_3$ | H | H | |
| 14.014 | H | H | H | NHCOCH$_2$CH$_3$ | H | H | |
| 14.015 | H | H | H | NHCHO | H | H | |
| 14.016 | H | H | H | CH(CH$_3$)CH$_2$CH$_3$ | H | H | |
| 14.017 | H | H | H | CH(CH$_3$)$_2$ | H | H | |
| 14.018 | Br | H | H | Cl | H | H | |
| 14.019 | Cl | H | H | Cl | H | H | |
| 14.020 | CH$_3$ | H | H | Cl | H | H | |
| 14.021 | CH$_3$ | 4'-CH$_3$ | H | H | H | H | |
| 14.022 | Cl | H | H | CH$_3$ | H | CH$_3$ | |
| 14.023 | H | H | 4-CH$_3$ | H | H | H | |
| 14.024 | H | H | 4-CH$_3$ | Cl | H | H | |
| 14.025 | CH$_3$ | 4'-CH$_3$ | H | Cl | H | H | |
| 14.026 | CH$_3$ | H | H | H | H | H | |
| 14.027 | OCH$_2$CH$_3$ | H | H | H | H | H | |
| 14.028 | OCH(CH$_3$)$_2$ | H | H | H | H | H | |
| 14.029 | CO$_2$CH$_3$ | H | H | H | H | H | |
| 14.030 | H | H | H | CF$_3$ | H | H | |
| 14.031 | Cl | H | H | CF$_3$ | H | H | |
| 14.032 | H | H | H | H | H | CH$_3$ | |
| 14.033 | Cl | H | H | C$_6$H$_5$ | H | H | |
| 14.034 | CH$_3$ | H | H | CF$_3$ | H | H | |
| 14.035 | Br | H | H | CF$_3$ | H | H | |
| 14.036 | CH$_2$CH$_3$ | H | H | CF$_3$ | H | H | |
| 14.037 | H | 4'-CF$_3$ | H | H | H | H | |
| 14.038 | H | 4'-CH$_2$OCH$_3$ | H | H | H | H | |
| 14.039 | H | 4'-CHCH$_3$ | H | H | H | H | |
| 14.040 | H | 4'-CH$_2$OCH$_3$ | H | Cl | H | H | |
| 14.041 | (CH$_2$)$_2$CH$_3$ | H | H | H | H | H | |
| 14.042 | (CH$_2$)$_2$CH$_3$ | H | H | Cl | H | H | |
| 14.043 | Cl | H | H | NO$_2$ | H | H | |
| 14.044 | H | H | H | OCH$_3$ | H | H | |
| 14.045 | Cl | H | H | OCH$_3$ | H | H | |

TABLE 15

I. 15

| No. | R¹ | R² | R³ | X¹ | X² | X³ | X⁴ | Phys. data |
|---|---|---|---|---|---|---|---|---|
| 15.001 | H | H | H | H | H | H | H | mp. 167–170° C. |
| 15.002 | CH₃ | H | H | H | H | H | H | mp. 136–137° C. |
| 15.003 | Cl | H | H | H | H | H | H | |
| 15.004 | Br | H | H | H | H | H | H | |
| 15.005 | OCH₃ | H | H | H | H | H | H | |
| 15.006 | H | H | H | CH₃ | CH₃ | H | H | |
| 15.007 | CH₃ | 4'-CH₃ | H | H | H | H | H | |
| 15.008 | H | H | 4-CH₃ | H | H | H | H | |
| 15.009 | H | H | H | CF₃ | H | H | H | |
| 15.010 | H | H | H | Cl | Cl | H | H | |
| 15.011 | Cl | H | H | Cl | Cl | H | H | |
| 15.012 | CH₂CH₃ | H | H | H | H | H | H | |
| 15.013 | OCH₂CH₃ | H | H | H | H | H | H | |

TABLE 16

I. 16

| No. | R¹ | R² | R³ | X⁴ | X¹ | X² | X³ | Phys. data |
|---|---|---|---|---|---|---|---|---|
| 16.001 | H | H | H | H | H | H | H | mp. 245–246° C. |
| 16.002 | H | H | H | CH₃ | H | H | H | mp. 165–170° C. |
| 16.003 | H | H | H | CH₃ | H | Cl | Cl | |
| 16.004 | H | H | H | CH₃ | H | CH₃ | CH₃ | |
| 16.005 | H | H | H | H | H | CH₃ | CH₃ | mp. >230° C. |
| 16.006 | H | H | H | H | CH₃ | H | H | |
| 16.007 | H | H | H | H | H | H | OCH₃ | |
| 16.008 | H | H | H | H | H | H | OCH₂CH₃ | |
| 16.009 | Cl | H | H | CH₃ | H | H | H | |
| 16.010 | CH₃ | H | H | CH₃ | H | H | H | |
| 16.011 | CH₃ | 4'-CH₃ | 4-CH₃ | CH₃ | H | H | H | |
| 16.012 | CH₃ | 4'-CH₃ | H | H | H | H | H | |
| 16.013 | Cl | Cl | H | CH₃ | H | H | H | |
| 16.014 | H | H | H | H | H | NO₂ | H | |
| 16.015 | H | H | H | H | H | CH₃ | H | |
| 16.016 | Cl | H | H | H | H | Cl | Cl | |
| 16.017 | OCH₃ | H | H | CH₃ | H | H | H | |
| 16.018 | Br | H | H | CH₃ | H | H | H | |
| 16.019 | CH₂CH₃ | H | H | CH₃ | H | H | H | |
| 16.020 | CH₂Cl | H | H | CH§ | H | H | H | |

Active ingredient table:

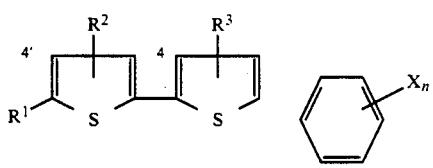

| No. | R¹ | R² | R³ | Xₙ | Mp [°C.] |
|---|---|---|---|---|---|
| 17.001 | CH₃ | H | H | H | 94–95 |
| 17.002 | H | H | H | 3-CH₃ | 70–72 |
| 17.003 | Cl | H | H | H | 128–132 |
| 17.004 | Br | H | H | H | 135–140 |
| 17.005 | H | 3'-CH₃ | H | H | 69–71 |
| 17.006 | H | H | H | 4-Cl | 165–167 |
| 17.007 | Cl | H | H | 4-Cl | 145–147 |

Active ingredient table:

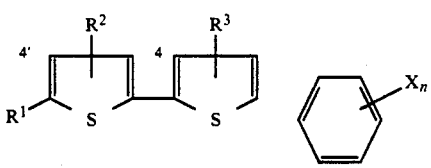

| No. | R¹ | R² | R³ | Xₙ | Mp [°C.] |
|---|---|---|---|---|---|
| 17.008 | H | 3'-CH₃ | H | 4-Cl | 79–81 |
| 17.009 | CH₃ | H | H | 4-Cl | 170–172 |
| 17.010 | H | H | H | 4-F | 141–142 |
| 17.011 | Cl | H | H | 4-F | 125–127 |
| 17.012 | CH₃ | H | H | 4-F | 142–144 |
| 17.013 | H | H | H | 4-CH₃ | 130–131 |
| 17.014 | H | H | H | 4-CF₃ | 174–176 |

-continued

Active ingredient table:

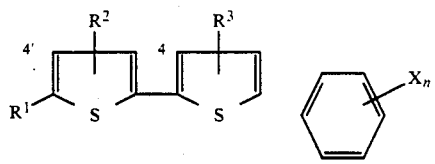

| No. | R¹ | R² | R³ | $X_n$ | Mp [°C.] |
|---|---|---|---|---|---|
| 17.015 | H | H | H | 4-CH₃O | 158–160 |
| 17.016 | CH₃ | H | H | 4-CH₃ | 100–101 |
| 17.017 | Br | H | H | H | 128–130 |
| 17.018 | CH₃ | H | H | 4-CH₃O | 160–162 |
| 17.019 | CH₂CH₃ | H | H | H | 79–81 |
| 17.020 | H | H | H | 3-F, 4-F | 140–142 |
| 17.021 | CH₃ | H | H | 3-Cl, 4-Cl | 126–128 |
| 17.022 | CH₃ | H | H | 4-CF₃ | 194–196 |
| 17.023 | CH₃ | H | H | 4-Br | 177–179 |
| 17.024 | H | H | H | 3-Cl | 98–100 |
| 17.025 | H | H | H | 4-CH₂CH₃ | 112–113 |
| 17.026 | H | H | H | 4-C(CH₃)₃ | 102–104 |
| 17.027 | H | H | H | 3-CF₃ | 90–92 |
| 17.028 | H | H | H | 3-OCF₂CHF₂ | 80–82 |
| 17.029 | H | H | H | 4-OCF₂CHF₂ | 144–146 |
| 17.030 | H | H | H | 4-OCF=CF₂ | 136–138 |
| 17.031 | Cl | H | H | 4-CH₃ | 145–147 |
| 17.032 | Cl | H | H | 4-CH₂CH₃ | 143–145 |
| 17.033 | CH₃ | H | H | 3-Cl | 98–99 |
| 17.034 | CH₃ | H | H | 4-OCHF₂ | 171–172 |
| 17.035 | CH₃ | H | H | 4-OCF₃ | 146–148 |
| 17.036 | NO₂ | H | H | H | 158–160 |
| 17.037 | COCH₃ | H | H | 4-SCH₃ | 144–149 |
| 17.038 | COH | H | H | 4-SCH₃ | 145–148 |
| 17.039 | CH₃ | H | H | 3-Cl, 4-Cl | 126–128 |
| 17.040 | CH₃ | H | H | 3-OCF₂CHF₂ | 96–98 |
| 17.041 | CH₃ | H | H | 4-SOCH₃ | 171–179 |
| 17.042 | CH₃ | H | H | 4-OC₆H₅ | 126–128 |
| 17.043 | CH₃ | H | H | NO₂ | 155–157 |
| 17.044 | CH₃ | H | H | 4-(4-Cl—C₆H₅) | |
| 17.045 | SCH₃ | H | H | H | 119–120 |
| 17.046 | CH₂CH₃ | H | H | 4-OCHF₂ | 157–158 |
| 17.047 | CH₃ | 4'-CH₃ | H | H | |

USE EXAMPLES

The herbicidal action of the bithienyl derivatives of the formula I on plant growth is demonstrated by the following greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated with the compounds suspended or emulsified in water. The application rates for postemergence treatment were 0.5 and 1.0 kg/ha. No covers were placed on the vessels in this method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants employed for the experiments were *Abutilon theophrasti, Amaranthus retroflexus, Bromus inermis, Digitaria sanguinalis, Linum usitatissimum, Oryza sativa, Solanum nigrum, Stellaria media* and *Veronica* spp.

Compounds 17.001 and 17.004, applied postemergence at a rate of 1.0 kg/ha, excellently combated unwanted broadleaved plants.

Compounds 1.001 and 1.002, applied postemergence at a rate of 0.5 kg/ha, excellently combated unwanted plants, and were well tolerated by rice.

Compound 2.002, applied postemergence at a rate of 1.0 kg/ha, had a herbicidal action on *Amaranthus retroflexus* and *Digitaria sanguinalis*.

We claim:

1. A bithienyl compound of the formula Ia

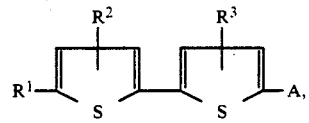

where the substituents have the following meanings:
R¹, R² hydrogen, halogen, nitro, formyl, C₁–C₆-alkyl, C₁–C₆-haloalkyl, C₃–C₈-cycloalkyl, C₃–C₈-cycloalkoxy, C₁–C₆-alkoxy, C₁–C₄-haloalkoxy, C₁–C₄-alkylthio, C₁–C₄-haloalkylthio, C₁–C₆-alkylcarbonyl which is unsubstituted or mono- to trisubstituted by halogen atoms, or C₃–C₆-cycloalkylcarbonyl which is unsubstituted or mono- to trisubstituted by halogen and/or C₁–C₄-alkyl, or C₁–C₆-alkoxycarbonyl and/or phenylcarbonyl; hydrogen, halogen, C₁–C₄-alkyl, C₁–C₄-alkoxy, C₁–C₄-alkylthio, C₁–C₄-haloalkyl or C₁–C₄-haloalkoxy;
is oxazol-2-yl, oxazol-5-yl, isoxazol-3-yl, or thiazol-2-yl and these ring systems may bear one or two halogen, C₁–C₆-alkyl, C₁–C₆-alkoxy, or C₁–C₆-alkylthio substituents each of the latter three substituents being unsubstituted or mono- to pentasubstituted by halogen and/or monosubstituted by C₁–C₄-alkoxy, C₁–C₄-haloalkyl, C₁–C₄-alkylthio, amino C₁–C₄-alkylamino or di-C₁–C₄-alkylamino;
-C₃–C₆-cycloalkyl or phenyl, each of which in turn is unsubstituted or mono- to pentasubstituted by halogen and/or mono- to trisubstituted by C₁–C₄-alkyl, C₁–C₄-haloakyl, C₁–C₄-alkoxy, C₁–C₄-haloalkoxy and/or C₁–C₄-alkylthio.

2. A herbicidal composition containing a carrier and a herbicidally effective amount of compound of the formula I.

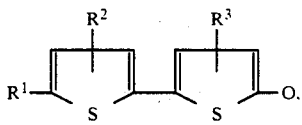

where
R$^1$, R$^2$ and R$^3$ have the meanings given in claim 1 and
B is, oxazol-2-yl, oxazol-5-yl, isoxazol-3-yl or thiazol-2-yl, and these ring systems may carry from one to two halogen atoms, C$_1$–C$_6$-alkyl, C$_1$–C$_6$-alkoxy, C$_1$–C$_6$-alkylthio, each of the latter three substituents being unsubstituted or mono- to pentasubstituted by halogen C$_1$–C$_4$-alkoxy, C$_1$–C$_4$-haloalkoxy, C$_1$–C$_4$-alkylthio, amino, C$_1$–C$_4$-alkylamino, or di-C$_1$–C$_4$-alkylamino;
C$_3$–C$_6$-cycloalkyl or phenyl, C$_1$–C$_4$-alkoxy, C$_1$–C$_4$-haloalkoxy, C$_1$–C$_4$-alkylthio, amino, C$_1$–C$_4$-alkylamino, or di-C$_1$–C$_4$-alkylamino; C$_3$–C$_6$-cycloalkyl or phenyl, each of which in turn may be mono- to pentasubstituted by halogen and/or mono- to trisubstituted by C$_1$–C$_4$-alkyl, C$_1$–C$_4$-haloalkyl, C$_1$–C$_4$-alkoxy, C$_1$–C$_4$-haloalkoxy and/or C$_1$–C$_4$-alkylthio.

3. A process for combating the growth of unwanted plants, wherein the unwanted plants and/or their habitat are treated with a herbicidally effective amount of a bithienyl derivative of the general formula I as set forth in claim 2.

4. A bithienyl compound of the formula Ia as defined in claim 1, wherein R$^1$, R$^2$ and R$^3$ are each hydrogen and A is (4-ethoxycarbonyl)-thiazol-2-yl.

5. A herbicidal composition as defined in claim 2, wherein R$^1$, R$^2$ and R$^3$ of the bithienyl compound are each hydrogen and B is (4-ethoxycarbonyl)-thiazol-2-yl.

6. A process for combating the growth of unwanted plants which comprises applying to the unwanted plants or their habitat, a herbicidally effective amount of a bithienyl compound as defined in claim 2, wherein R$^1$, R$^2$ and R$^3$ of the bithienyl compound are each hydrogen and B is (4-ethoxycarbonyl)-thiazol-2-yl.

* * * * *

UNITED STATES PATENT AND TRADEMARK OFFICE
CERTIFICATE OF CORRECTION

PATENT NO. : 5,158,598
DATED : October 27, 1992
INVENTOR(S) : KOBER et al.

It is certified that error appears in the above-identified patent and that said Letters Patent is hereby corrected as shown below:

Col. 35, claim 2, lines 1-7

" 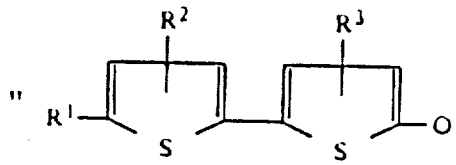 "

should read

-- 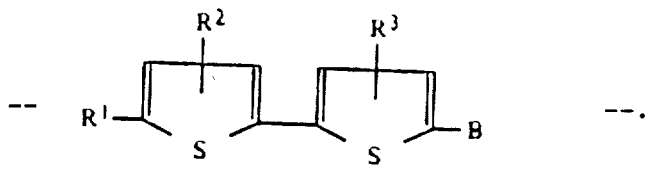 --.

Signed and Sealed this

Sixteenth Day of November, 1993

*Attest:*

BRUCE LEHMAN

*Attesting Officer*     *Commissioner of Patents and Trademarks*